United States Patent
Chien et al.

(10) Patent No.: US 9,545,213 B2
(45) Date of Patent: Jan. 17, 2017

(54) ELECTRODE PATCH AND PHYSIOLOGICAL SIGNAL DEVICE

(71) Applicants: KINPO ELECTRONICS, INC., New Taipei (TW); CAL-COMP ELECTRONICS & COMMUNICATIONS COMPANY LIMITED, New Taipei (TW)

(72) Inventors: Jen-Chien Chien, New Taipei (TW); Wen-Chung Cheng, New Taipei (TW)

(73) Assignees: KINPO ELECTRONICS, INC., New Taipei (TW); CAL-COMP ELECTRONICS & COMMUNICATIONS COMPANY LIMITED, New Taipei (TW)

( * ) Notice: Subject to any disclaimer, the term of this patent is extended or adjusted under 35 U.S.C. 154(b) by 236 days.

(21) Appl. No.: 14/506,750

(22) Filed: Oct. 6, 2014

(65) Prior Publication Data

US 2015/0366506 A1 Dec. 24, 2015

(30) Foreign Application Priority Data

Jun. 24, 2014 (TW) .............................. 103121645 A

(51) Int. Cl.
| | | |
|---|---|---|
| *A61B 5/0408* | (2006.01) | |
| *A61B 5/0492* | (2006.01) | |
| *A61B 5/00* | (2006.01) | |

(52) U.S. Cl.
CPC ......... *A61B 5/04085* (2013.01); *A61B 5/0492* (2013.01); *A61B 5/6833* (2013.01)

(58) Field of Classification Search
CPC . A61B 5/0422; A61B 5/0492; A61B 5/04085; A61B 5/0408; A61B 5/049277
See application file for complete search history.

(56) References Cited

U.S. PATENT DOCUMENTS 4,398,545 A * 8/1983 Wilson ................. A61N 1/0456
607/152
7,486,980 B2 * 2/2009 Lin ..................... A61B 5/04087
600/391

(Continued)

FOREIGN PATENT DOCUMENTS

| TW | 200612888 A | 5/2006 |
| TW | 200820941 A | 5/2008 |
| TW | M417898 U | 12/2011 |

OTHER PUBLICATIONS

Office Action dated Oct. 23, 2014 of the corresponding Taiwan patent application No. 103121645.

*Primary Examiner* — Lee S Cohen
(74) *Attorney, Agent, or Firm* — Chun-Ming Shih; HDLS IPS Services

(57) ABSTRACT

An electrode patch and physiological signal device are disclosed. The physiological signal device includes an electrode patch and a physiological signal unit. The physiological signal unit has a conductive pad, and the electrode patch includes a flexible sheet having a first surface and a second surface opposite from each other, a conductive pad is disposed on the first surface, a conductive gel covers a portion of the conductive pad and a conductive area is exposed; the conductive gel penetrates through the flexible sheet and is exposed on the second surface; the second surface of the electrode patch contacts with the physiological signal unit, and the conductive gel is electrically connected to the conductive pad. The physiological signal unit is electrically connected to a charging device via the conductive area of the electrode patch. Thereby, the physiological signal unit can be placed on the charging device directly for charging.

13 Claims, 7 Drawing Sheets

(56) References Cited

U.S. PATENT DOCUMENTS

| | | |
|---|---|---|
| 7,819,812 B2 | 10/2010 | John et al. |
| 8,449,469 B2 | 5/2013 | Banet et al. |
| 2001/0047127 A1 | 11/2001 | New et al. |
| 2004/0088036 A1 | 5/2004 | Gilbert |
| 2010/0274099 A1 | 10/2010 | Telfort et al. |
| 2011/0213272 A1 | 9/2011 | Telfort et al. |
| 2011/0213273 A1 | 9/2011 | Telfort et al. |
| 2013/0150698 A1 | 6/2013 | Hsu et al. |

* cited by examiner

ELECTRODE PATCH AND PHYSIOLOGICAL SIGNAL DEVICE

BACKGROUND OF THE INVENTION

Technical Field

The technical field relates to a physiological signal device, in particular, to a rechargeable physiological signal device and an electrode patch thereof.

Description of Related Art

A conventional physiological signal monitoring device typically uses an electrocardiographic signal capturing device to capture the physiological signal of the monitored subject. In addition, an external auxiliary instrument is used for transmitting the physiological signal data of the patient monitored to a medical unit or a monitoring center in order to be used as a reference basis for analyzing the conditions of the patient.

However, for some of the chronic illness, the physiological signal needs to be controlled and monitored for a longer period of time in order to effectively reduce the risk of the occurrence of the illness by monitoring the physiological signal. To facilitate long time wearing on human body without affecting the daily life, there are selling wireless and small size of physiological signal devices in the market currently. Specifically, OK-bandage type of wireless physiological signal device utilizes an electrode patch with a conductive adhesive tape to be adhered onto the small size of physiological signal device, and then, the conductive adhesive tape is used for attaching onto the human body to perform the measurements.

In addition, a power source of the currently existing portable physiological signal device mainly comes from the use of a button cell battery. Since the battery needs to be replaced frequently causes inconvenience of use, there has been a solution proposing to be configured additionally a connection port at the lateral side of the housing of the physiological signal device for connecting a power transmission wire from the connection port to a charging device, thus relatively increases the mechanical complexity and the overall thickness.

SUMMARY OF THE INVENTION

Thus, one of the exemplary embodiments provides an electrode patch and a physiological signal device. The physiological signal device can be charged directly on a charging device such that its convenience of use is increased while being environment friendly.

One of the exemplary embodiments provides an electrode patch attached onto a physiological signal unit and placed on a charging device for charging; the electrode patch comprising a flexible sheet, a conductive pad and a conductive gel. The flexible sheet includes a first surface and a second surface opposite from each other; the conductive pad is disposed on the first surface of the flexible sheet; the conductive gel covers a portion of the conductive pad and allowing a conductive area to be exposed; the conductive gel is arranged corresponding to the conductive pad and penetrating through the flexible sheet in order to be exposed at the second surface of the flexible sheet; wherein the physiological signal unit is electrically connected to the charging device via the conductive area of the electrode patch.:

One of the exemplary embodiments provides a physiological signal device placed on a charging device for charging. A physiological signal unit includes a plurality of conductive contact points. A flexible sheet includes a first surface and a second surface opposite from each other; conductive pads are disposed on the first surface of the flexible sheet respectively and arranged corresponding to locations of the conductive contact points; conductive gels cover a portion of the conductive pads respectively and allowing a conductive area to be exposed; the conductive gels are arranged corresponding to the conductive pads and penetrating through the flexible sheet in order to be exposed at the second surface of the flexible sheet; wherein the second surface of the flexible sheet is attached onto the physiological signal unit; the conductive gels exposed at the second surface are electrically connected to the conductive contact points; the physiological signal unit is electrically connected to the charging device via the conductive area of the flexible sheet.

One of the exemplary embodiments provides an electrode patch and a physiological signal device. When the conductive gels of the first surface of the electrode patch is attached onto the human body, the physiological signal unit is able to capture the physiological signal of the human body from the conductive contact point, and the controller is able to process the physiological signal of the human body. In addition, when the conductive contact point of the physiological signal unit is electrically connected to the charging electrode of the charging device via the conductive area of the first surface of the electrode patch, the controller is able to determine the charging power on the conductive contact point at this time rather than the physiological signal of the human body and to control the charging unit to guide the charging power form the conductive contact point to the battery in order to charge the battery.

According to the above of the disclosure the exemplary embodiments, the charging device can be used to directly charge the physiological signal unit, therefore it can be increased convenience without being replaced frequently the battery.

Furthermore, since the physiological signal unit of one of the exemplary embodiments allows its internal battery to be charged directly via the conductive contact points, there is no need to be configured additionally a charging socket on the physiological unit such that further cost of the device can be reduced. In addition, the conductive area of the conductive pad has a greater outer diameter than that of the conductive contact point, which allows the physiological signal unit to be fitted onto various types of charging device with different specifications such that greater flexibility and convenience of use for the user can be achieved according to an exemplary embodiment.

DETAILED DESCRIPTION OF THE INVENTION

Figure 1:
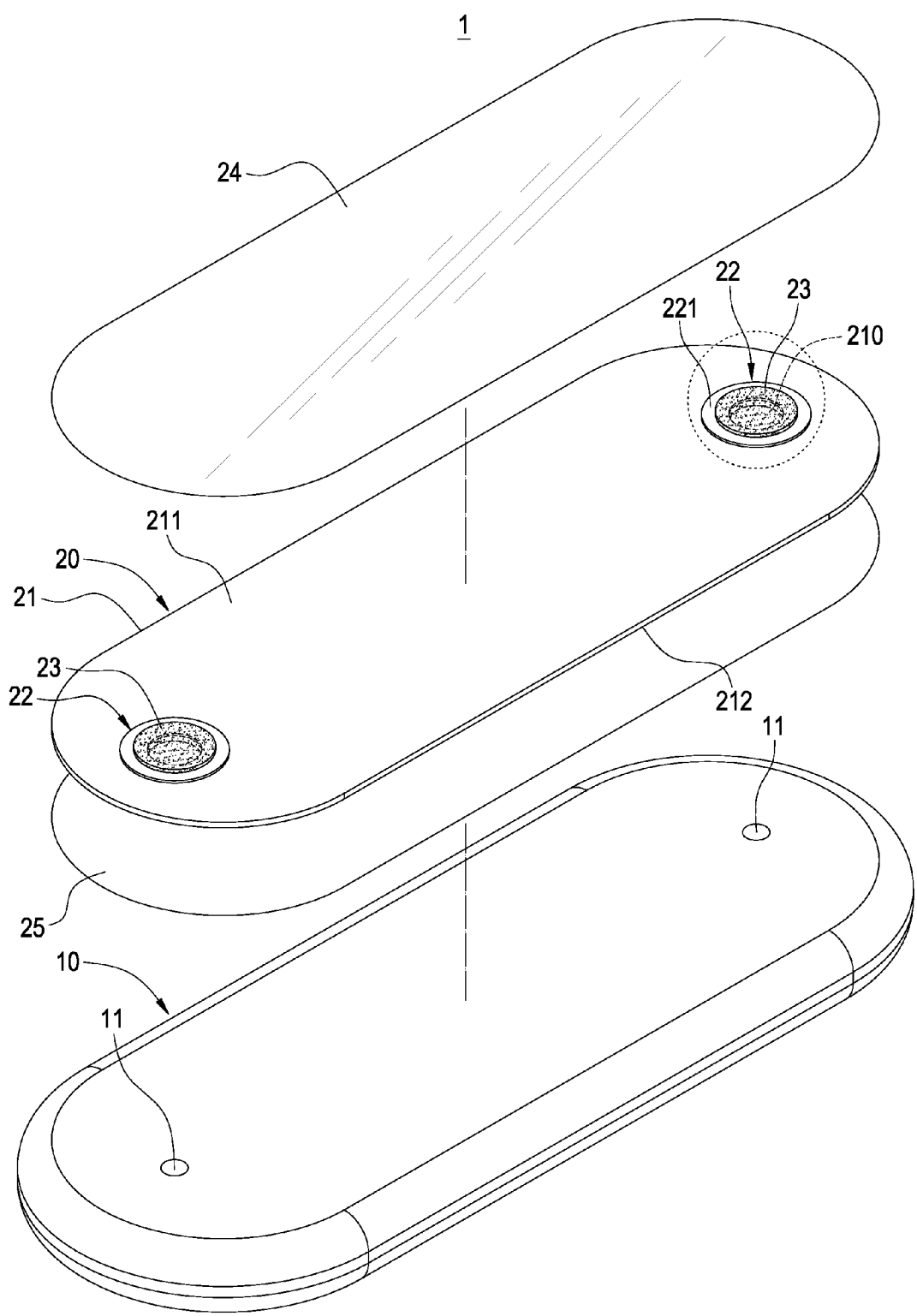
FIG. 1 is a perspective view of an assembly of the physiological signal unit and the electrode patch according to an exemplary embodiment.

The following provides a detailed description of the present preferred embodiments along with the accompanied drawings; however, it shall be understood that the accompanied drawings are provided for illustrative purposes only, which shall not be treated as limitations of the disclosure. Please refer to FIG. 1 to FIG. 3, respectively showing a perspective view of an assembly of the physiological signal unit and the electrode patch, a partially enlarged perspective view of the electrode patch and a cross sectional view of the electrode patch according to an exemplary embodiment. The exemplary embodiment discloses a physiological signal device 1, and the physiological signal device 1 comprises a physiological signal unit 10 and an electrode patch 20. The electrode patch 20 is attached onto the physiological signal unit 10 and used for measuring a physiological signal of the human body.

The physiological signal unit 10 includes a plurality of conductive contact points 11. The electrode patch 20 comprises a flexible sheet 21, at least one conductive pad 22 and at least one conductive gel 23. The flexible sheet 21 includes a first surface 211 and a second surface 212 opposite from each other. The conductive pad 22 is disposed on the first surface 211 of the flexible sheet 21 and arranged corresponding to a location of the conductive contact point 11.

In addition, the conductive gel 23 covers a portion of the conductive pad 22 and allows a conductive area 221 to be exposed. Moreover, the conductive gel 23 is arranged corresponding to the conductive pad 22 and penetrating through the flexible sheet 21 in order to be exposed at the second surface 212.

In this embodiment, the flexible sheet 21 can be a flexible sheet body made of a nonwoven fabric, a woven fabric or a knitted fabric; however, the exemplary embodiment is not limited to such types only. The conductive pad 22 is made of a conductive metal, such as silver. The conductive gel 23 is made of a material consisting of a 2-Hydroxyethyl Methacrylate (HEMA). Furthermore, the electrode patch 20 can further comprise a protective layer 24 and an adhesive layer 25. The protective layer 24 covers the first surface 211; in addition, the adhesive layer 25 is adhered onto the second surface 212. Preferably, the protective layer 24 is a release paper for protecting the first surface of the flexible sheet 21 prior to its uses; the adhesive layer 25 is a double-sided tape for adhering onto the second surface 212 of the flexible sheet 21 in order to allow the flexible sheet 21 to be adhered onto the physiological signal unit 10.

In one of an exemplary embodiments, the flexible sheet 21 includes an opening hole 210 arranged corresponding to the location of the conducive contact point 11 and penetrating through the first surface 211 and the second surface 212, and the conductive gel 23 is disposed inside the opening hole 210 and extends to the first surface 211 within a certain range. During an actual practice, if the flexible sheet 21 is made of a permissible material, such as the aforementioned nonwoven fabric, woven fabric or knitted fabric, then there is no need to provide the opening hole 210 on the flexible sheet 21 as the conductive gels 23 are able to penetrate into the flexible sheet 21 from the first surface 211 and to be further retained on the second surface 212. Moreover, the conductive pads 22 are arranged corresponding to a hole edge of the opening hole 210 and extend outward therefrom.

Figure 4:
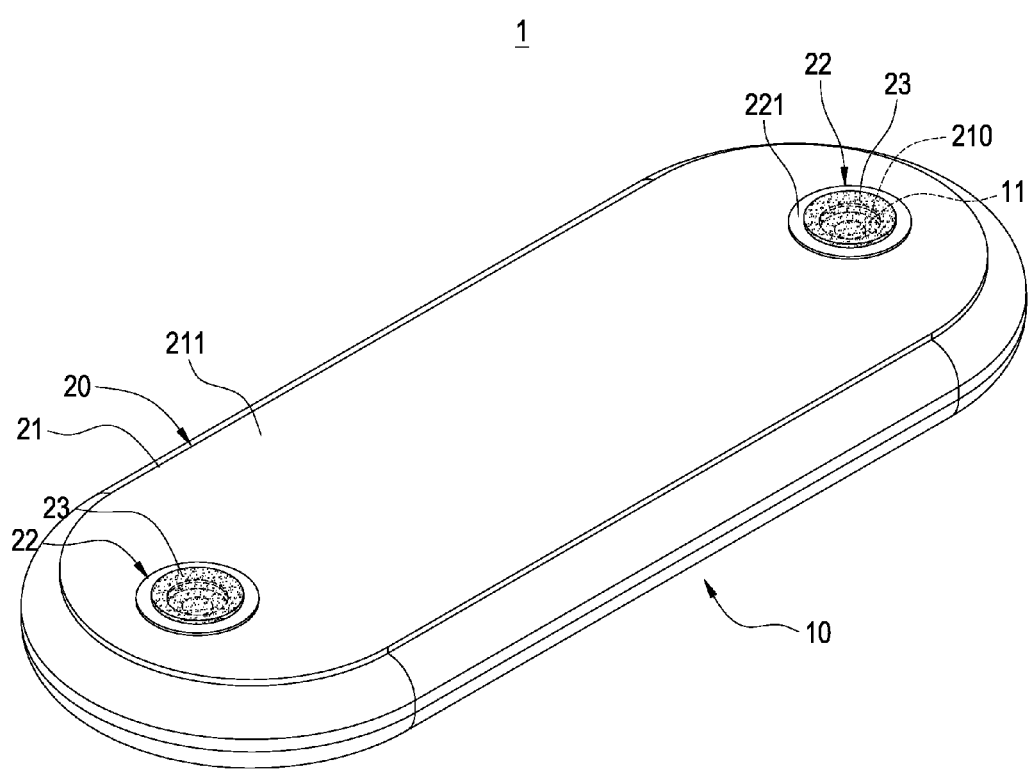
FIG. 4 is a perspective view showing the physiological signal unit and the electrode patch according to an exemplary embodiment.
Figure 5:
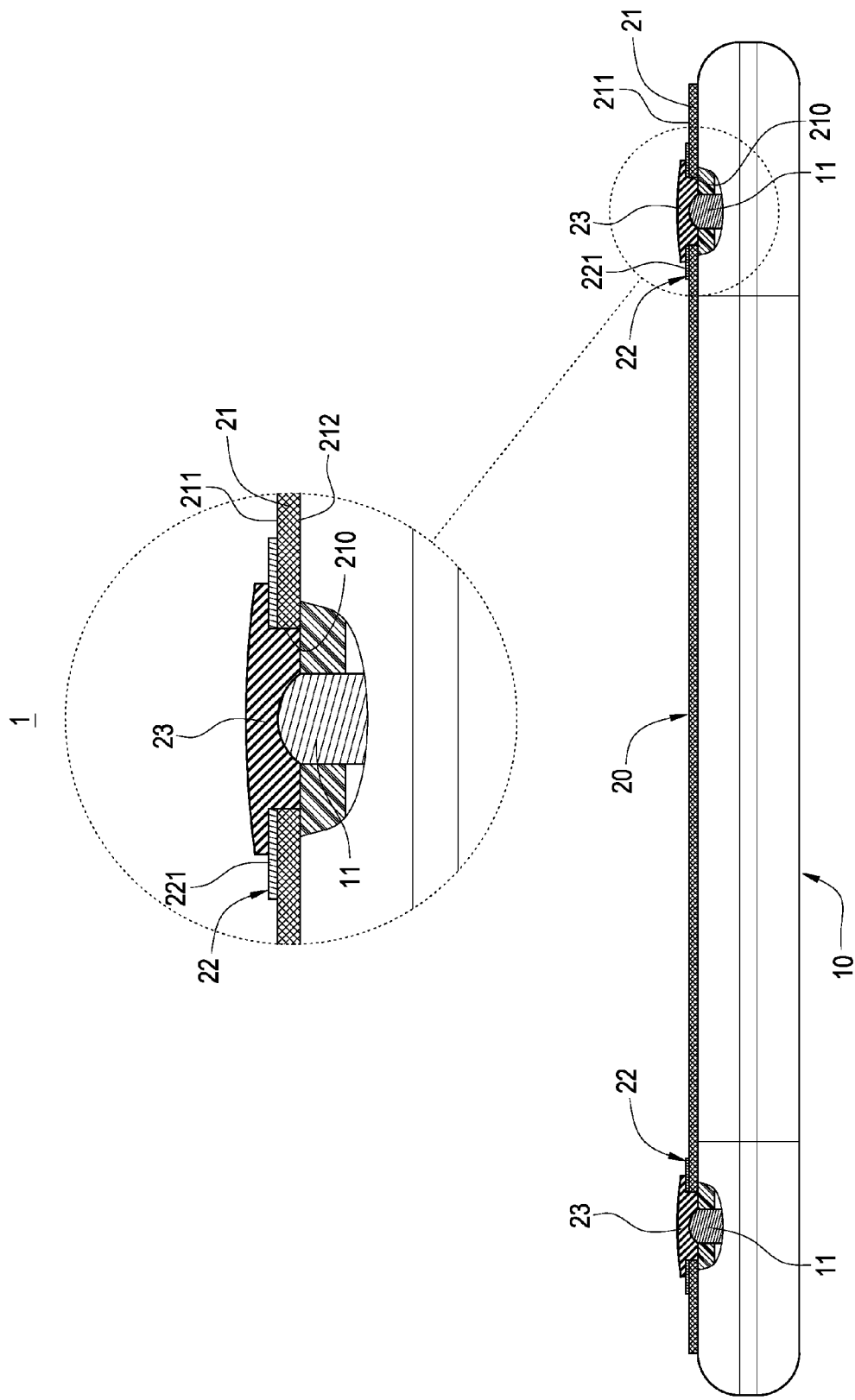
FIG. 5 is a cross sectional view showing the physiological signal unit and the electrode patch after being assembled according to an exemplary embodiment.

Please refer further to FIG. 4 and FIG. 5, respectively showing an outer view and a cross sectional view of the physiological signal unit and the electrode patch according to an exemplary embodiment after being assembled. During the use of the physiological signal unit 10, first, the electrode patch 20 is attached onto the physiological unit 10. In this embodiment, the second surface 212 of the electrode patch 20 is adhered onto the physiological signal unit 10 via the adhesive layer 25 (not shown in the figure). At this time, the conductive gels 23 exposed on the second surface 212 are able to form electrical connections with the conductive contact points 11 of the physiological signal unit 10, following which the conductive gels 23 on the first surface 211 of the electrode patch 20 are attached onto the human body. Accordingly, the physiological signal unit 10 can then be utilized to capture the physiological signal of the human body.

Figure 6:
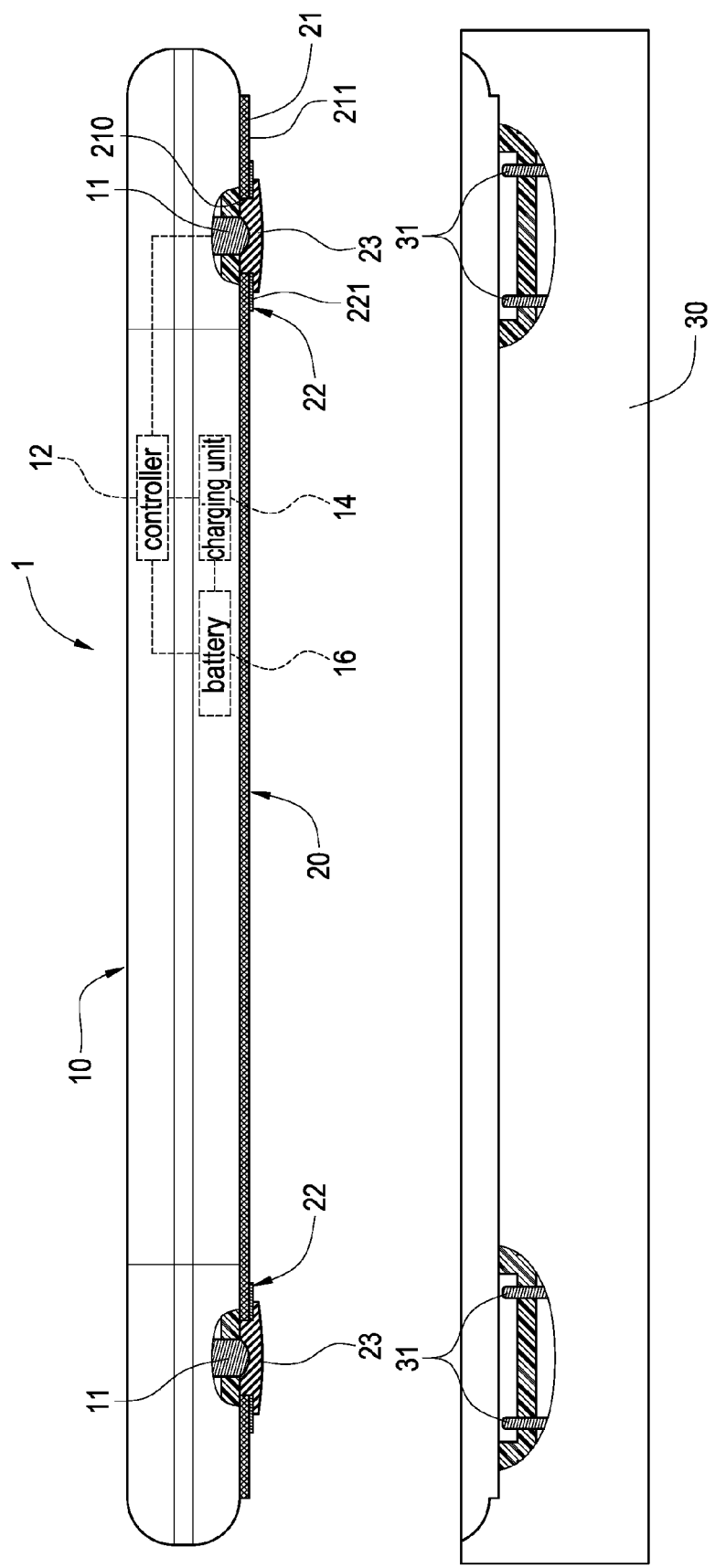
FIG. 6 is an illustration showing a state of use of the physiological signal unit and its electrode patch along with the charging device according to an exemplary embodiment.
Figure 7:
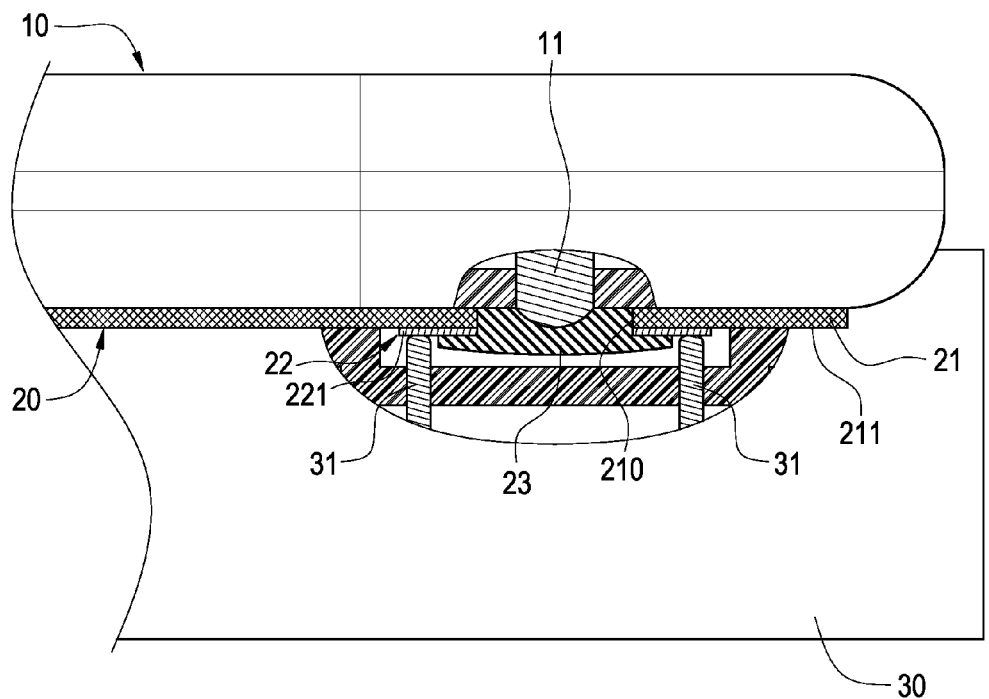
FIG. 7 is an illustration showing the physiological signal unit and its electrode patch being attached to the charging device according to an exemplary embodiment.

Please refer to FIG. 6 and FIG. 7, respectively showing illustrations of a state of use and attachments of the physiological signal unit and its electrode patch according to an exemplary embodiment along with a charging device. The physiological signal unit 10 according to an exemplary embodiment having the electrode patch 20 attached thereto is placed onto a charging device 30 for charging. In this embodiment, the charging device 30 includes at least one charging electrode 31 exposed thereon; in another embodiment, the charging device 30 can include a plurality of charging electrodes 31 exposed thereon.

The assembly of the electrode patch 20 is as described above, in which the second surface 212 is attached onto the physiological signal unit 10. In addition, in order to charge the physiological signal unit 10, the physiological signal unit 10 is electrically connected to the charging electrode 31 of the charging device 30 via the conductive area 221, referring to the conductive area 221 exposed as only a portion of the conductive pad 22 is covered by the conductive gel 23, on the first surface 211 of the electrode patch 20. Accordingly, the charging device 30 is able to directly charge the physiological signal unit 10 via the electrode patch 20.

Please refer to FIG. 6 again. The physiological signal unit 10 includes a controller 12, a charging unit 14 and a battery 16 operatively connected to one another, and the controller 12 and the charging unit 14 are electrically connected to the conducive contact points 11. When the conductive gels 23 on the first surface 211 of the electrode patch 20 are attached onto the human body, the physiological signal unit 10 is able to capture the physiological signal of the human body via the conductive contact points 11, and the controller 12 is able to process the physiological signal of the human body. When the conductive contact points 11 of the physiological signal unit 10 are electrically connected to the charging electrodes 31 of the charging device 30 via the conductive area 221 on the first surface 211 of the electrode patch 20, the controller 12 is able to determine that the charging power delivered to the conductive contact points 11 at this time is not physiological signal of the human body and is able to control the charging unit 14 to guide the charging power 11 from the conductive contact points 11 to the battery 16 in order to charge the battery 16.

Since the physiological signal unit 10 is able to charge the internal battery 16 via the conductive contact points 11, there is no need to provide additional charging socket on the physiological signal unit 10 such that its cost can be further reduced. Moreover, the conductive area 221 of the conductive pad 22 has a greater outer diameter than that of the conductive contact point 11 such that it allows the physiological signal unit 10 to be fitted onto various types of charging devices 30 with different specifications and greatly increases the flexibility and convenience of the device utilized by the user.

Figure 8:
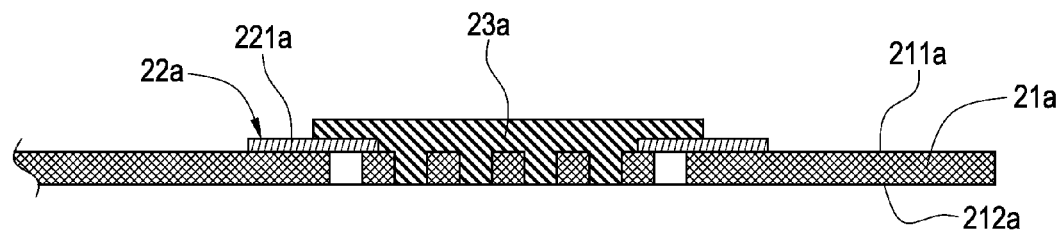
FIG. 8 shows another embodiment of the electrode patch according to an exemplary embodiment.

Please refer further to FIG. 8, showing another embodiment of the electrode patch according to an exemplary embodiment. In this embodiment, the electrode patch 20a comprises a flexible sheet 21a, a plurality of conductive pads 22a and a plurality of conductive gels 23a. The flexible sheet 21a comprises a first surface 211a and a second surface 212a opposite from each other. The conductive pads 22a are disposed on the first surface 211a of the flexible sheet 21a. Each one of the conductive gels 23a covers a portion of the conductive pads 22a and allows a conductive area 221a to be exposed thereon.

The present embodiment differs from the previous embodiment mainly in that the flexible sheet 21a includes no opening hole. The flexible sheet 21a is made of a permissible material, such as a nonwoven fabric, a woven fabric and a knitted fabric. The conductive gels 23a are able to penetrate into the flexible sheet 21a from the first surface 211a and to be further retained on the second surface 212a.

Figure 9:
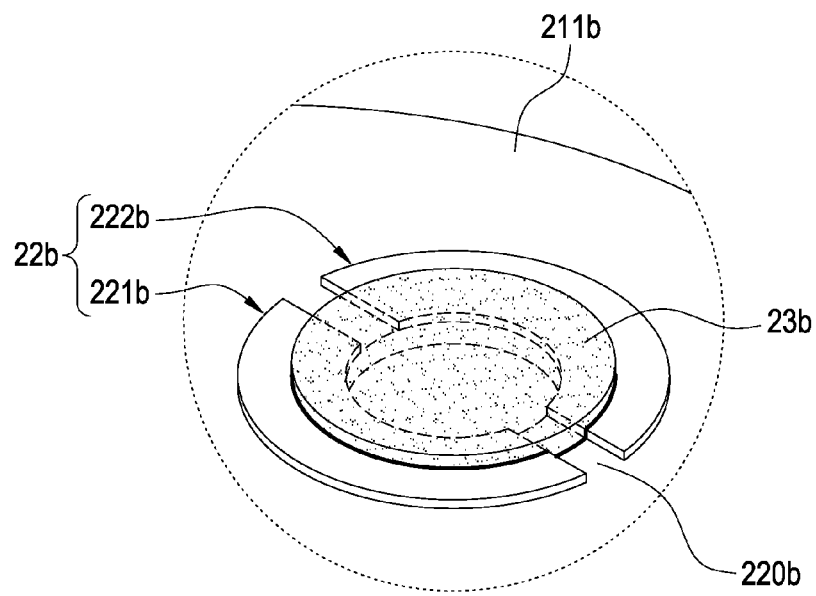
FIG. 9 shows still another embodiment of the electrode patch according to an exemplary embodiment.
Figure 10:
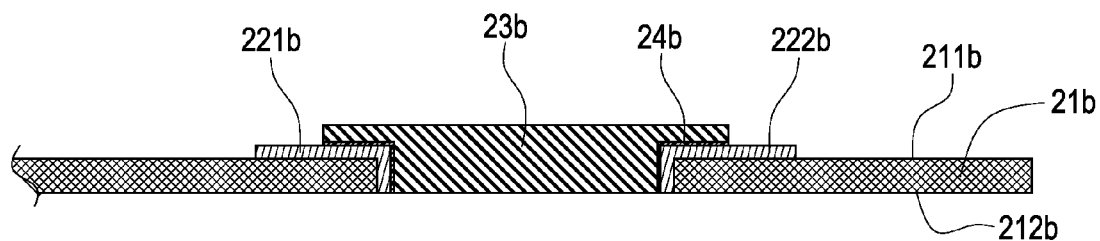
FIG. 10 is a cross sectional view of another embodiment of the electrode patch of according to an exemplary embodiment.

Please refer further to FIG. 9 and FIG. 10, showing still another embodiment of the electrode patch according to an exemplary embodiment. In this embodiment, the electrode patch 20b comprises a flexible sheet 21b, a plurality of conductive pads 22b, at least one conductive gel 23b and an insulation layer 24b. The flexible sheet 21b comprises a first surface 211b and a second surface 212b opposite from each other.

The present embodiment differs mainly in that a number of the conductive pads 22b corresponding to a charging electrode of the charging device is plural. The conductive pads 22b are spaced apart from each other and disposed adjacent to each other on the first surface 211b of the flexible sheet 21b to be exposed on the second surface 212b, and a gap 220b is formed between the adjacent conductive pads 22b. The conductive gel 23b partially covers the conductive pads 22b and correspondingly allowing a plurality of conductive areas 221b, 222b spaced apart from each other and disposed adjacent to each other to be exposed thereon; wherein the insulation layer 24b is further disposed on the portion of the surface of the conductive pads 22b covered by the conductive gel 23b. The arrangement of the insulation 24b is able to prevent the conductive areas 221b, 222b from establishing electrical connections with each other.

Figure 2:
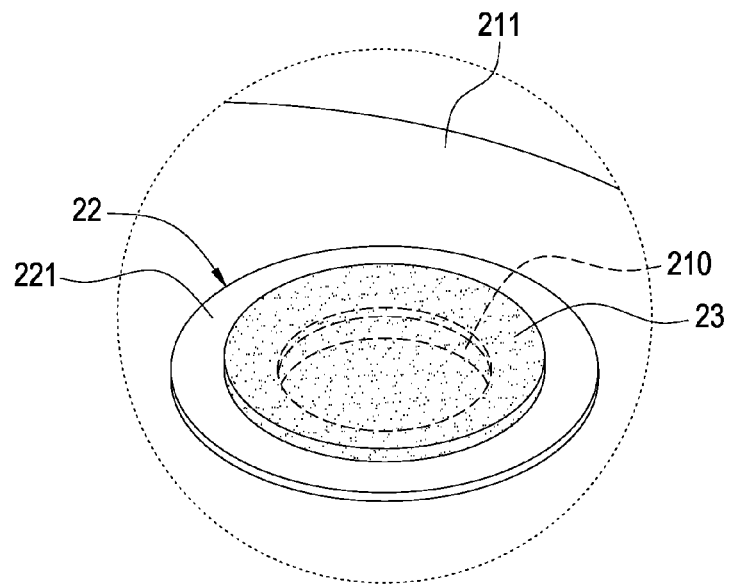
FIG. 2 is a partially enlarged perspective view of the electrode patch according to an exemplary embodiment.
Figure 3:
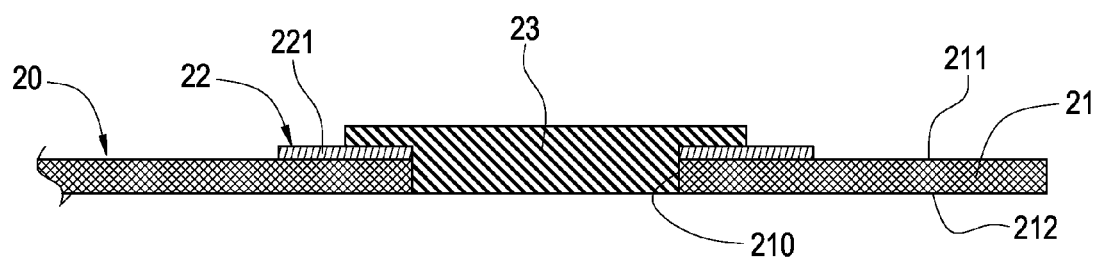
FIG. 3 is a cross sectional view of the electrode patch according to an exemplary embodiment.

It shall be noted that in FIG. 9 and FIG. 10, the location of one charging electrode of the charging electrodes utilized by the corresponding electrode patch 20b can be charging electrodes of different polarities in addition to that they are disposed on one side of the physiological signal unit only for charging. Accordingly, the conductive pads 22b are arranged corresponding to the charging electrodes of different polarities to be of different polarities as well; therefore, part of the conductive pads 22b is covered by one of the conductive gels 23b and corresponds to the conductive areas 221b, 222b exposed and spaced apart from each other as well as dispose adjacent to each other thereon. The conductive areas 221b, 222b correspond to electrodes of different polarities, and the physiological signal unit is electrically connected to the charging electrodes of different polarities via the conductive areas 221b, 222b of the flexible sheet 21b respectively. Similarly, the insulation layer is also disposed between the portion of conductive pads 22b covered by the conductive gels 23b and the conductive gels 23b. Furthermore, the charging electrodes 31 of the physiological signal unit 10 utilized by the electrode patch 20 correspondingly, as shown in FIG. 2 and FIG. 3, are arranged on two sides of the physiological signal unit 10; however, for an actual practice, they can still be modified according to the actual needs.

The above provides descriptions on the preferred embodiment according to an exemplary embodiment only, which shall not be treated as limitations according to an exemplary embodiment. Any equivalent modifications without deviating from the spirit according to an exemplary embodiment shall be deemed to be within the scope according to an exemplary embodiment.

What is claimed is:

1. An electrode patch, which is adapted to be attached onto a physiological signal unit and placed on a charging device for charging; the electrode patch comprising:
   a flexible sheet having a first surface and a second surface opposite from each other;
   a conductive pad disposed on the first surface of the flexible sheet; and
   a conductive gel covering a portion of the conductive pad to expose a conductive area of the conductive pad at the first surface of the flexible sheet, the conductive gel distributed corresponding to the conductive pad and penetrating through the flexible sheet in order to be exposed at the second surface of the flexible sheet from the conductive area; wherein the physiological signal unit is adapted to be electrically connected to the charging device via the conductive area of the electrode patch.

2. The electrode patch according to claim 1, wherein the flexible sheet includes an opening hole penetrating through the first surface and the second surface; the conductive gel is disposed inside the opening hole and spreads to the first surface.

3. The electrode patch according to claim 2, wherein the conductive pad is disposed at a hole edge of the opening hole and extends outward therefrom.

4. The electrode patch according to claim 1, further comprising a protective layer and an adhesive layer; the protective layer covers the first surface; the adhesive layer is adhered onto the second surface.

5. The electrode patch according to claim 1, wherein a number of the conductive pad corresponding to a charging electrode of the charging device is plural, and the plurality of conductive pads are spaced apart from each other and disposed adjacent to each other on the first surface of the flexible sheet, and a gap is formed between adjacent conductive pads; the conductive gel partially covers the plurality of conductive pads and correspondingly allowing a plurality of conductive areas spaced apart from each other and disposed adjacent to each other to be exposed thereon.

6. The electrode patch according to claim 5, wherein an insulation layer is disposed between the conductive gel and the portion of the plurality of conductive pads covered by the conductive gel in order to prevent the plurality of the conductive areas from establishing electrical connections with each other.

7. A physiological signal device, which is adapted to be placed on a charging device for charging, comprising:
   a physiological signal unit having a plurality of conductive contact points;

a flexible sheet having a first surface and a second surface opposite from each other;

a plurality of conductive pads disposed on the first surface of the flexible sheet respectively and arranged corresponding to locations of the plurality of conductive contact points; and a plurality of conductive gels covering a portion of each one of the conductive pads respectively to expose a conductive area of the conductive pads at the first surface of the flexible sheet; the plurality of conductive gels distributed corresponding to the plurality of conductive pads and penetrating through the flexible sheet in order to be exposed at the second surface of the flexible sheet from the conductive area;

wherein the second surface of the flexible sheet is attached onto the physiological signal unit; the plurality of conductive gels exposed at the second surface are electrically connected to the plurality of conductive contact points; the physiological signal unit is adapted to be electrically connected to the charging device via the conductive area of the flexible sheet.

8. The physiological signal device according to claim 7, wherein the flexible sheet includes a plurality of opening holes disposed corresponding to locations of the plurality of conductive contact points and penetrating through the first surface and the second surface; the plurality of conductive gels are disposed inside the plurality of opening holes and spread to the first surface.

9. The physiological signal device according to claim 8, wherein the plurality of conductive pads are respectively disposed at hole edges of the plurality of opening holes correspondingly and extend outward therefrom.

10. The physiological signal device according to claim 7, wherein the electrode patch further comprises a protective layer and an adhesive layer; the protective layer covers the first surface; the adhesive layer is adhered onto the second surface.

11. The physiological signal device according to claim 7, wherein the physiological signal unit further includes a controller, a charging unit and a battery operatively connected to each other, and the controller and the charging unit are electrically connected to the plurality of conducive contact points; wherein when the plurality of conductive contact points of the physiological signal unit use the conductive area of the first surface of the electrode patch to be electrically connected to the charging device, the controller controls the charging unit and guides a charging power from the plurality of conductive contact points to the battery.

12. The physiological signal device according to claim 7, wherein a charging electrode location of the charging device includes charging electrodes of different polarities; the plurality of conductive pads are configured to be of different polarities corresponding to the different polarities of the plurality of charging electrodes; the plurality of conductive pads are spaced apart from each other and disposed adjacent to each other on the first surface of the flexible sheet, and a gap is formed between the adjacent conductive pads; one of the plurality of conductive gels partially covers the plurality of conductive pads and correspondingly allowing a plurality of conductive areas spaced apart from each other and disposed adjacent to each other to be exposed thereon; wherein the physiological signal unit is electrically connected to the plurality of charging electrodes of different polarities respectively via the plurality of conductive areas of the flexible sheet.

13. The physiological signal device according to claim 12, wherein an insulation layer is disposed between the conductive gels and the portion of the plurality of conductive pads covered by the conductive gels in order to prevent the plurality of conductive areas from establishing electrical connections with each other.

\* \* \* \* \*